US010781692B2

(12) United States Patent
Francois et al.

(10) Patent No.: US 10,781,692 B2
(45) Date of Patent: Sep. 22, 2020

(54) METHOD AND SYSTEM FOR ANALYZING ROCK SAMPLES

(71) Applicant: Geoservices Equipements, Roissy en France (FR)

(72) Inventors: Matthias Francois, Roissy-en-France (FR); Josselin Kherroubi, Clamart (FR); Alexis He, Clamart (FR); Tetsushi Yamada, Clamart (FR); Quentin Corlay, Roissy-en-France (FR); Karim Bondabou, Roissy-en-France (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 207 days.

(21) Appl. No.: 15/972,630

(22) Filed: May 7, 2018

(65) Prior Publication Data
US 2019/0338637 A1  Nov. 7, 2019

(51) Int. Cl.
| | |
|---|---|
| *G06K 9/00* | (2006.01) |
| *E21B 49/00* | (2006.01) |
| *G06T 7/11* | (2017.01) |
| *E21B 49/08* | (2006.01) |
| *G01N 21/17* | (2006.01) |

(Continued)

(52) U.S. Cl.
CPC ............ *E21B 49/005* (2013.01); *E21B 49/08* (2013.01); *G01N 21/17* (2013.01); *G01N 33/24* (2013.01);

(Continued)

(58) Field of Classification Search
CPC ................. E21B 49/005; E21B 49/08; G01N 2021/1776; G01N 21/17; G01N 33/24;
(Continued)

(56) References Cited

U.S. PATENT DOCUMENTS

| | | | |
|---|---|---|---|
| 2009/0208106 A1* | 8/2009 | Dunlop .............. | G06K 9/00664 382/173 |
| 2009/0254281 A1* | 10/2009 | Hruska .................. | G01V 11/00 702/7 |

(Continued)

OTHER PUBLICATIONS

Search and Examination Report issued in European patent application 19173029.0 dated Oct. 8, 2019, 6 Pages.
(Continued)

*Primary Examiner* — Xin Jia

(57) ABSTRACT

A method for determining a property of a geological formation based on an optical image of rock samples taken from the formation is presented therein. The image comprises a plurality of pixels and the method comprises defining windows in the image, each window comprising predetermined number of pixels and being of a predetermined shape. The method also includes, for each window, extracting a rockprint value representative of the window. A rockprint comprises indicators for characterizing a texture of the window. The method also includes classifying the windows into categories of a predetermined set. Each category is representative of one type of rock and the classification is based on a comparison of the rockprint value of each window with rockprint values of images of reference rock samples for each category. Based on the classification, the method then includes determining the at least one property of the geological formation, ie the quantification of each type of rock in the sample.

20 Claims, 10 Drawing Sheets

(51) Int. Cl.
*G01N 33/24* (2006.01)
*G06K 9/62* (2006.01)
*G06T 7/40* (2017.01)

(52) U.S. Cl.
CPC ............... *G06K 9/627* (2013.01); *G06T 7/11* (2017.01); *G06T 7/40* (2013.01); *G01N 2021/1776* (2013.01); *G06T 2207/10004* (2013.01); *G06T 2207/10056* (2013.01); *G06T 2207/10061* (2013.01); *G06T 2207/30181* (2013.01)

(58) Field of Classification Search
CPC ........... G06K 2009/6295; G06K 9/342; G06K 9/4642; G06K 9/627; G06T 2207/10004; G06T 2207/10056; G06T 2207/10061; G06T 2207/30181; G06T 7/11; G06T 7/40
See application file for complete search history.

(56) References Cited

U.S. PATENT DOCUMENTS

2010/0303348 A1* 12/2010 Tolliver .................... G06T 7/90
382/164
2013/0308831 A1* 11/2013 Dvorkin ............... G01N 33/341
382/109
2015/0324993 A1* 11/2015 Stein ........................ G06T 7/10
382/164

OTHER PUBLICATIONS

Perez et al., Ore grade estimation by feature selection and voting using boundary detection in digital image analysis, International Journal of Mineral Processing, Amsterdam, NL, Jul. 10, 2011, pp. 28-36.

* cited by examiner

METHOD AND SYSTEM FOR ANALYZING ROCK SAMPLES

BACKGROUND

The disclosure relates to a method and system for analyzing rock samples, such as cuttings obtaining during drilling of a geological formation.

During the drilling process of an oil well or of a well of another effluent—in particular gas, vapour or water—, cuttings are brought to the surface after they have been cut from the formation by drilling mud circulating in the wellbore.

It is known to carry out analysis of the rock cuttings brought to the surface. Such analysis allows the creation of a detailed record of the geologic formations of a borehole, in function of the well bore depth and may allow to derive information for instance concerning the lithology of the formation.

Among several known analyses, it is common to take at least an image of a sample of cuttings, in particular via a high resolution microscope.

Generally, this image is analysed by a geologist to determine the nature of the cuttings so as to determine the lithology of the geological formation from which the rock sample is extracted. Such work takes a substantial amount of time and is generally performed in a lab away from the drilling installation. Further, such work is highly subjective as it is based on human observation.

SUMMARY

The present disclosure relates to a method for determining a property of a geological formation based on an optical image of rock samples taken from the formation. The image comprises a plurality of pixels and the method comprises defining windows in the image, each window comprising predetermined number of pixels and being of a predetermined shape. The method also includes, for each window, extracting a rockprint value representative of the window. A rockprint comprises indicators for characterizing a texture of the window. The method also includes classifying the windows into categories of a predetermined set. Each category is representative of one type of rock and the classification is based on a comparison of the rockprint value of each window with rockprint values of images of reference rock samples for each category. Based on the classification, the method then includes determining the at least one property of the geological formation, ie the quantification of each type of rock in the sample.

The method according to the disclosure enables to identify the nature of cuttings coming from the borehole without any human intervention via a robust and reliable method based on a database of reference images, without necessitating any specific preparation of the sample such as separating cuttings on the image.

The method according to the disclosure therefore enables to provide the service of lithology identification in real-time or real near-time at a substantially reduced cost.

The disclosure also relates to a corresponding system for determining at least a property of a geological formation based on an optical image of rock samples taken from the formation. The image comprises a plurality of pixels. The system comprises a calculator comprising modules having processors, and the calculator is configured to define a plurality of windows in the image, each window comprising predetermined number of pixels and being of a predetermined shape. The calculator is also configured to extract a rockprint value representative of the window for each window. The rockprint comprises at least one indicator for characterizing a texture of the window. It is further configured to classify the windows of the image into categories of a predetermined set, wherein each category is representative of one type of rock, and the classification is based on a comparison of the rockprint value of each window with rockprint values of images of reference rock samples for each category. Based on the classification, the calculator is also configured to determine the at least one property of the geological formation, ie the quantification of each type of rock in the sample.

The disclosure also relates to a computer program for determining at least a property of a geological formation based on an optical image of rock samples taken from the formation. The image comprises a plurality of pixels. The computer program comprises machine readable instructions to define a plurality of windows in the image, each window comprising predetermined number of pixels and being of a predetermined shape. It also comprises instructions to extract a rockprint value representative of the window for each window. The rockprint comprises at least one indicator for characterizing a texture of the window. It further comprises instructions to classify the windows of the image into categories of a predetermined set, wherein each category is representative of one type of rock, and the classification is based on a comparison of the rockprint value of each window with rockprint values of images of reference rock samples for each category. Based on the classification, the computer program also comprises instructions to determine the at least one property of the geological formation, ie the quantification of each type of rock in the sample.

Even though the benefits of the method have been described above in relationship with the drill cuttings, the method may be applied to any type of rock samples, such as cores extracted from the formation.

BRIEF DESCRIPTION OF THE DRAWINGS

Various aspects of this disclosure may be better understood upon reading the following detailed description and upon reference to the drawings in which.

DETAILED DESCRIPTION

One or more specific embodiments of the present disclosure will be described below. These described embodiments are examples of the presently disclosed techniques. Additionally, in an effort to provide a concise description of these embodiments, some features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would still be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.'

Figure 1:
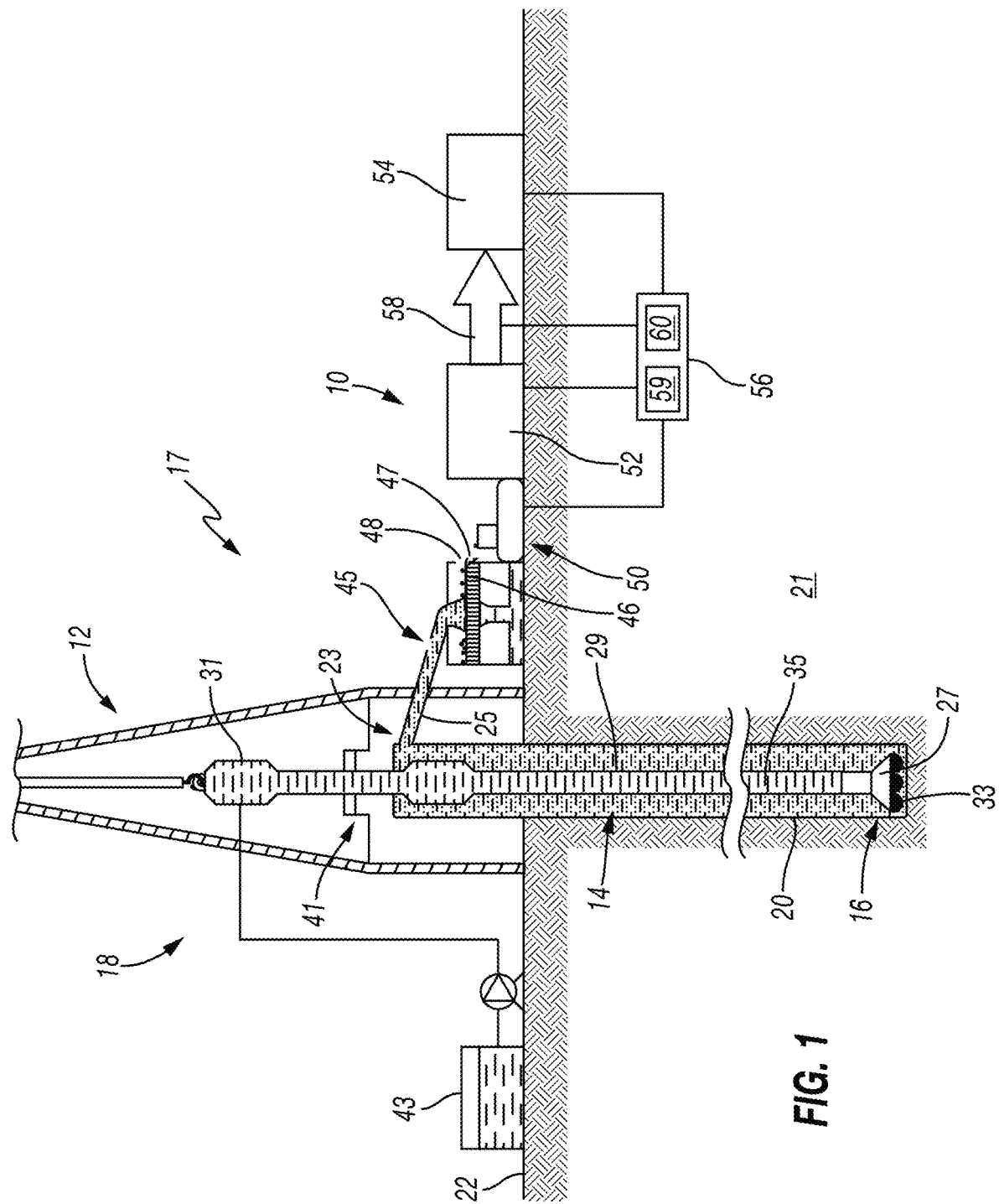
FIG. 1 is a schematic diagram of a drilling installation comprising a system according an embodiment of the disclosure

An installation 12 for drilling a borehole is described on FIG. 1.

Such an installation 12, comprises a rotary drilling tool 14 drilling a cavity 16; a surface installation 18, where drilling pipes are placed in the cavity 16.

A borehole 20, delimiting the cavity 16, is formed in the substratum 21 by the rotary drilling tool 14. At the surface 22, a well head 23 having a discharge pipe 25 closes the borehole 20.

The drilling tool 14 comprises a drilling head 27, a drill string 29 and a liquid injection head 31.

The drilling head 27 comprises a drill bit 33 for drilling through the rocks of the substratum 21. It is mounted on the lower portion of the drill string 29 and is positioned in the bottom of the drilling pipe 20.

The drill string 29 comprises a set of hollow drilling pipes. These pipes delimit an internal space 35 which makes it possible to bring a drilling fluid from the surface 22 to the drilling head 27. To this end, the liquid injection head 31 is screwed onto the upper portion of the drill string 29.

The drilling fluid is a drilling mud, in particular a water-based or oil-based drilling mud.

The surface installation 18 comprises a support 41 for supporting the drilling tool 14 and driving it in rotation, an injector 43 for injecting the drilling fluid and a shale shaker 45.

The injector 43 is hydraulically connected to the injection head 31 in order to introduce and circulate the drilling fluid in the inner space 35 of the drill string 29.

The shale shaker 45 collects the drilling fluid charged with drilling residues, known as cuttings, said drilling fluid flowing out from the discharge pipe 25. The shale shaker comprises a sieve 46 allowing the separation of the solid drilling cuttings 47 from the drilling mud. The shale shaker 45 also comprises an outlet 48 for evacuating the drilling cuttings 47.

Cuttings obtained at the outlet 48 have been cut from the formation when drilling and may be useful in order to evaluate the formation and characterize one or several of its properties, such as its mineralogy, lithology, porosity, density, etc. It is known to perform analysis on the cuttings in order to derive at least some of these properties from such analysis.

The disclosure relates to a method and system for analyzing cuttings exiting the borehole via the outlet 48 for instance. The system may be situated at the rig site, in the vicinity of the shale shaker 45 as is disclosed on FIG. 1 or in a cabin a few hectometers from the shale shaker or away from the rig site, in a laboratory.

The system according to the disclosure comprises a sampler for collecting the cuttings at the outlet 48. The sampler is here a container 49. It also comprises an optical imaging device 54 for taking at least an image of a sample of cuttings. The imaging device (also called imager in the following of the specification) is for instance an optical or electronic microscope or a camera.

The system may also comprise a preparation unit 52 for instance for washing, drying, separating, etc. the cuttings of the sample. However, this preparation unit is optional and cuttings may be imaged right after having been sampled. It is to be noted that the cuttings do not need to be separated from each other before being imaged.

In the embodiment shown on FIG. 1, the rock sample is automatically sampled, transferred to the preparation device 52 and then to imaging device 54 via a conveyor 50 and a transport device 58. The preparation and/or imaging may be performed automatically via any appropriate devices commanded via an appropriate sequence of actions of devices 52, 54. Alternatively, any conveyance device may also be used for transporting the cuttings.

The system also comprises a calculator 56 connected at least to the imager in order to receive images taken by the imager. The calculator may be a personal computer for instance. It may comprise a storage unit for storing programs and a processor for executing one or several programs as well as a communication module for communication at least with the imager. The calculator 56 may comprise an analysis module 59 in order to analyze the image taken by the imager as will be described below. It may also optionally comprise a control unit 60 for controlling the preparation and imaging of the sample in which case it is also able to communicate with the conveyor 50, the preparation device 52, the imager 54 and the transport device 58. It may also communicate with other modules at the rig site for instance in order to determine the depth at which the sample comes from, which is a well-known computation based on lag time. The calculator may be situated in the vicinity of the imager or remotely from the imager. It may also comprise several modules situated at different locations, for instance one situated in the vicinity of the imager and one situated remotely from the imager. Each module includes at least a processor for executing computer programs and a memory for storing the programs including instructions enabling to perform all or part of the method.

It is to be noted that the system according to FIG. 1 is only an exemplary system. It has been described when the rock sample is a sample of cuttings that is automatically handled. However, in another embodiment, the sample may be manually collected, and transferred by an operator to a cabin or to a lab and imaged, and optionally prepared, there. In such embodiment, the system according to the disclosure may also comprises only an imager for taking an image of the rock sample and a calculator as described above, in its simplest implementation. Such system may analyze any type of rock samples, such as drill cuttings, or cores, for instance.

Figure 2A:
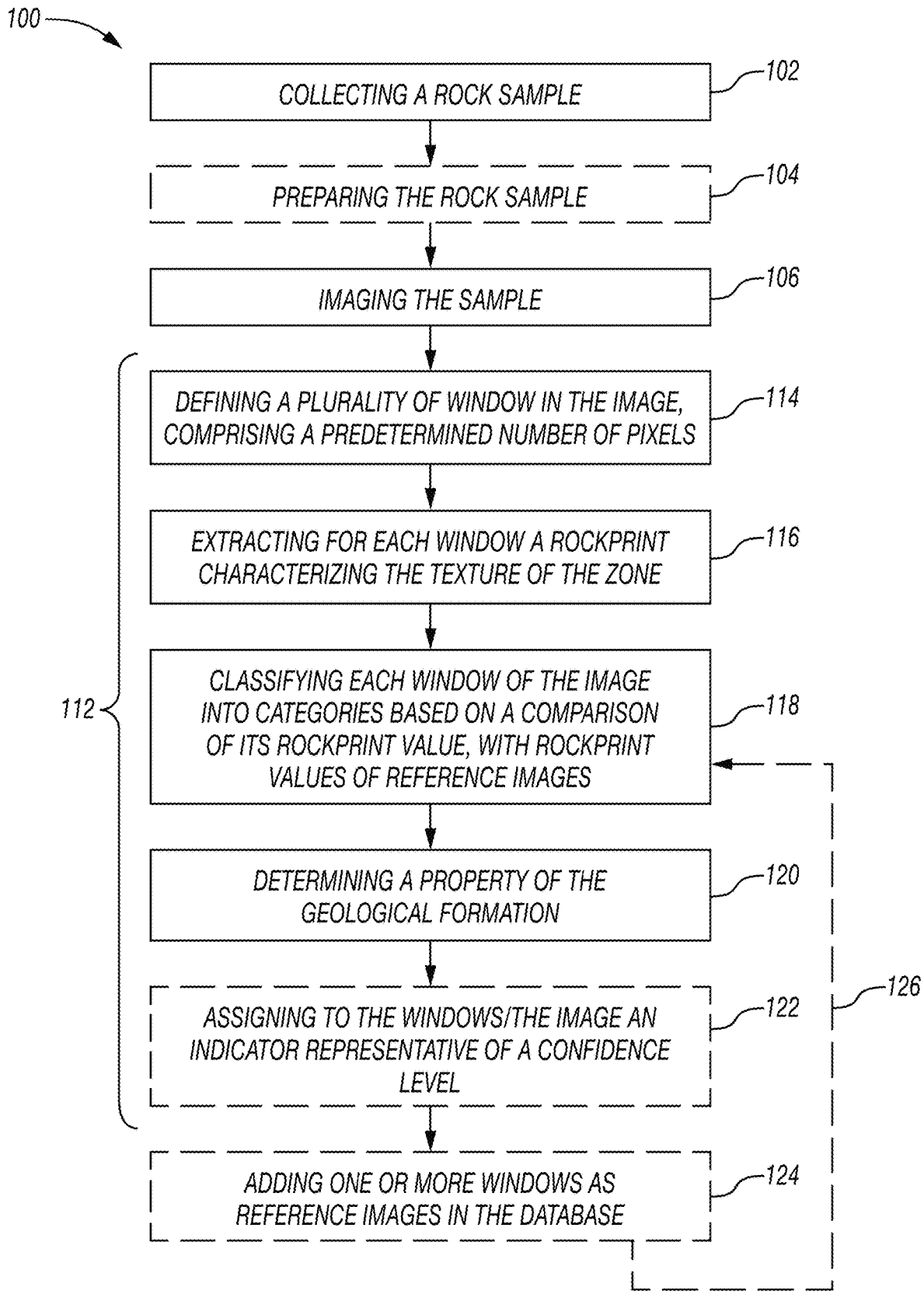
FIG. 2A is a flow diagram of an embodiment of the method according to an embodiment of the disclosure.

The method 100 according to an embodiment of the disclosure will now be described in accordance with FIG. 2. The method first comprises collecting a sample of rock (block 102), for instance a sample of drill cuttings at the outlet 48 of the shale shaker 45. As indicated earlier, collection may be performed in any manner, manually or automatically, in a bag or in a container, etc. Then the method may then comprise an optional operation of preparing the sample for the imaging (block 104), for instance at the preparation unit 52. The preparation may comprise sequentially washing, rinsing, drying, sieving the sample of rocks or at least one of these operations.

Figure 3:
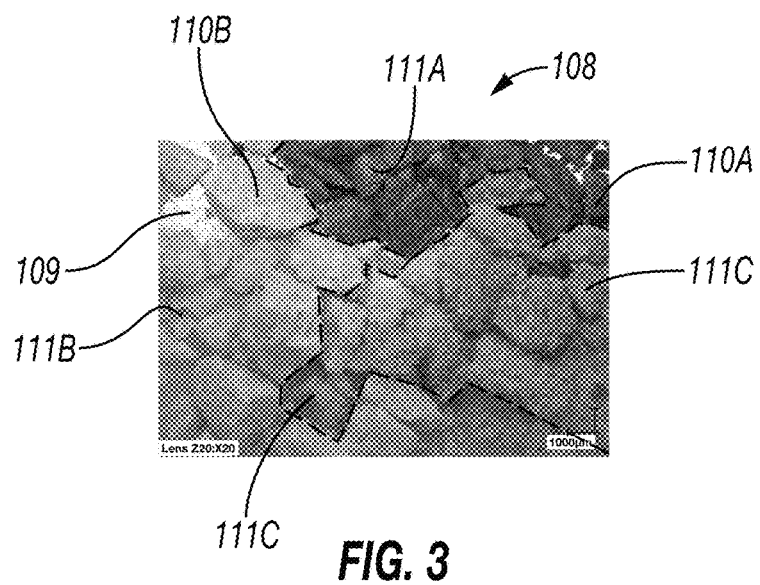
FIG. 3 is an image of cuttings obtained at the exit of the wellbore.

Then, the method comprises taking an image of the rock sample (block 106) with the optical imaging device 54 such as the optical or electronic microscope. "Optical image" is an image obtained by illuminating a sample with a light spectra and detecting the spectrum transmitted by the sample. The examples below are given with cameras detecting visible light spectrum but the same methods may be applied to an image taken with infrared (IR) or ultraviolet (UV) camera detecting light in UV or IR domains. An exemplary image 108 is shown on FIG. 3. This image shows cuttings 110A, 110B distributed on the whole image. As indicated above, the image may be taken so that the cuttings are in contact with each other eliminating the risk for a specific preparation process including cuttings separation.

The method then comprises analyzing the image (block 112). The analysis is performed by one or more modules of the calculator, in particular by executing with a processor a computer program stored on a memory of a module.

Figure 4:
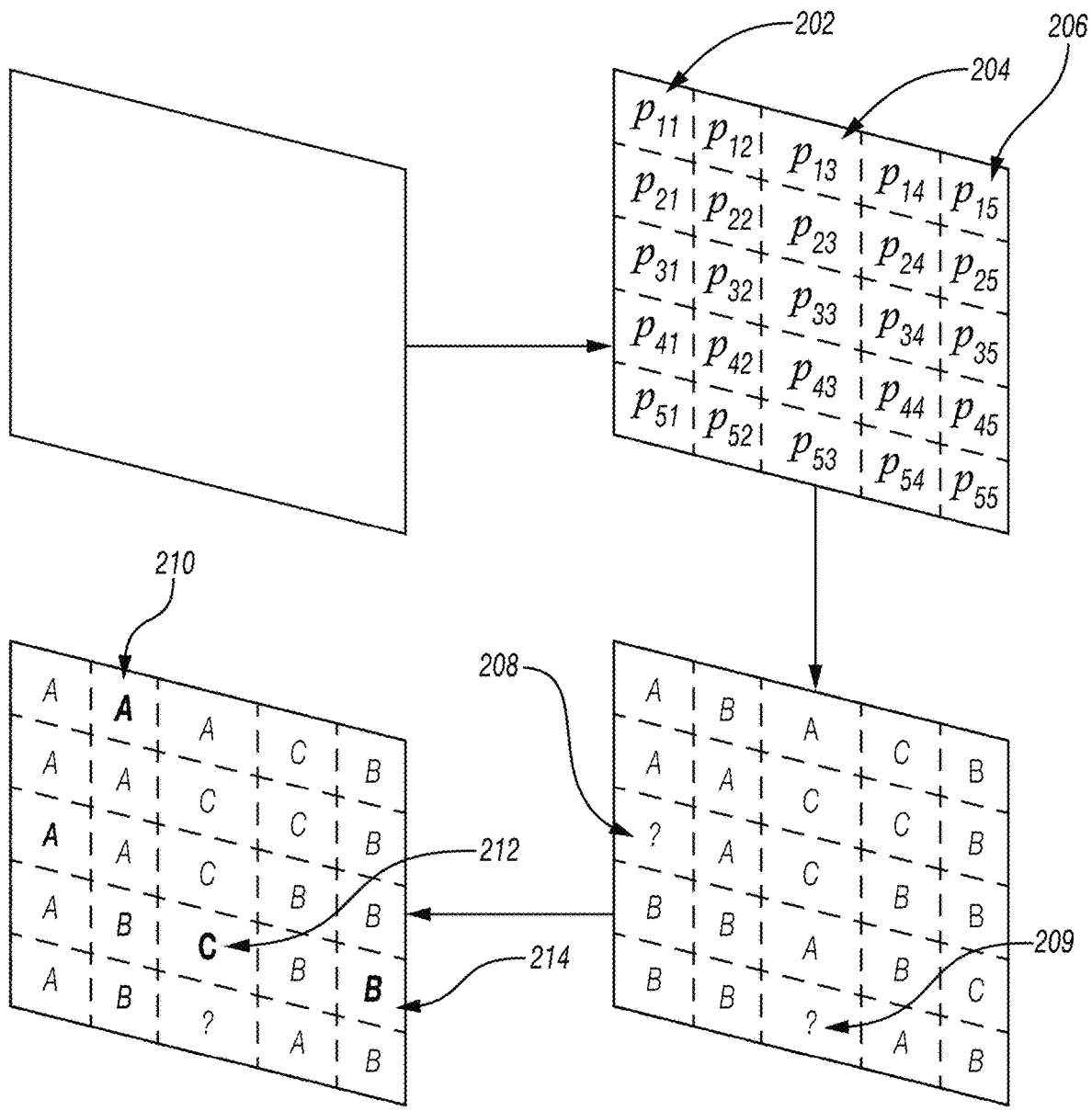
FIG. 4 is a schematic representation of several operations of the method of FIG. 2A.

A first embodiment of the analysis of the image in also represented more schematically on FIG. 4. In the first embodiment, the method comprises defining a plurality of windows 202, 204, 206 in the image (block 114), wherein each window comprises predetermined number of pixels. The windows may also be of a predetermined shape. They may be defined on the image so that one pixel belongs to one window only or they may be overlapping, so that one pixel belongs to two distinct windows. The windows may for instance be adjacent squares of n*n pixels. For instance, in FIG. 4, the windows are defined so that the image contains 5 rows of 5 five windows each, each window being a squared window. This is however a simple example and many other shapes or arrangement may be chosen for the windows.

The method comprises afterwards extracting, for each window, a rockprint value representative of the window (block 116). The rockprint comprises at least one indicator for characterizing the window. Each indicator may characterize in particular the texture of the window, ie the arrangement of colors and intensities within the window. The rockprint value for each window is designated as Pij, wherein i identifies the row and j the column is which the window is situated.

One indicator for a predetermined window may for instance be a statistical value of a predetermined feature of each pixel of the window. A feature may be for instance a coordinate of the pixel in a predetermined coordinate space of the image or a coordinate representative of a response of each pixel to a predetermined filter, such as a Gabor filter. Known coordinate spaces for image are for instance (R, G, B) ie (Red, Green, Blue) or (H, S, B), ie (Hue, Saturation, Brightness). In the latter, it is reminded that hue is a coordinate representative of the color itself while saturation is the expression of the color intensity/purity and brightness represents the brilliance. Examples of such statistical indicators are average (or median) and variance (or standard deviation) of the hue of all the pixels of the windows. When the feature is representative of a pixel only, two indicators may be computed representative of the feature for the whole window, such as representative of its value (the average or median) and of its distribution (such as variance or standard deviation) in the window.

Another example of indicator representative of the window may be a wavelet energy obtained by applying a wavelet transform to the window or a Haralick's indicator. For such indicator only one value characterizing the window may be obtained.

Generally, the rockprint comprises a combination of several indicators, such as a vector having different coordinates, each corresponding to an indicator. The plurality of indicators may be for instance associated to features representative of the response of each pixel of the window to a plurality of distinct filters and/or of the transform of the window according to different wavelets.

Once the rockprint value has been computed for each window, the method includes classifying the windows of the image into categories of a predetermined set of categories, each being representative of one type of rock (block 118). A flowchart showing the different operations that may occur during classification is shown on FIG. 2B.

Figure 2B:
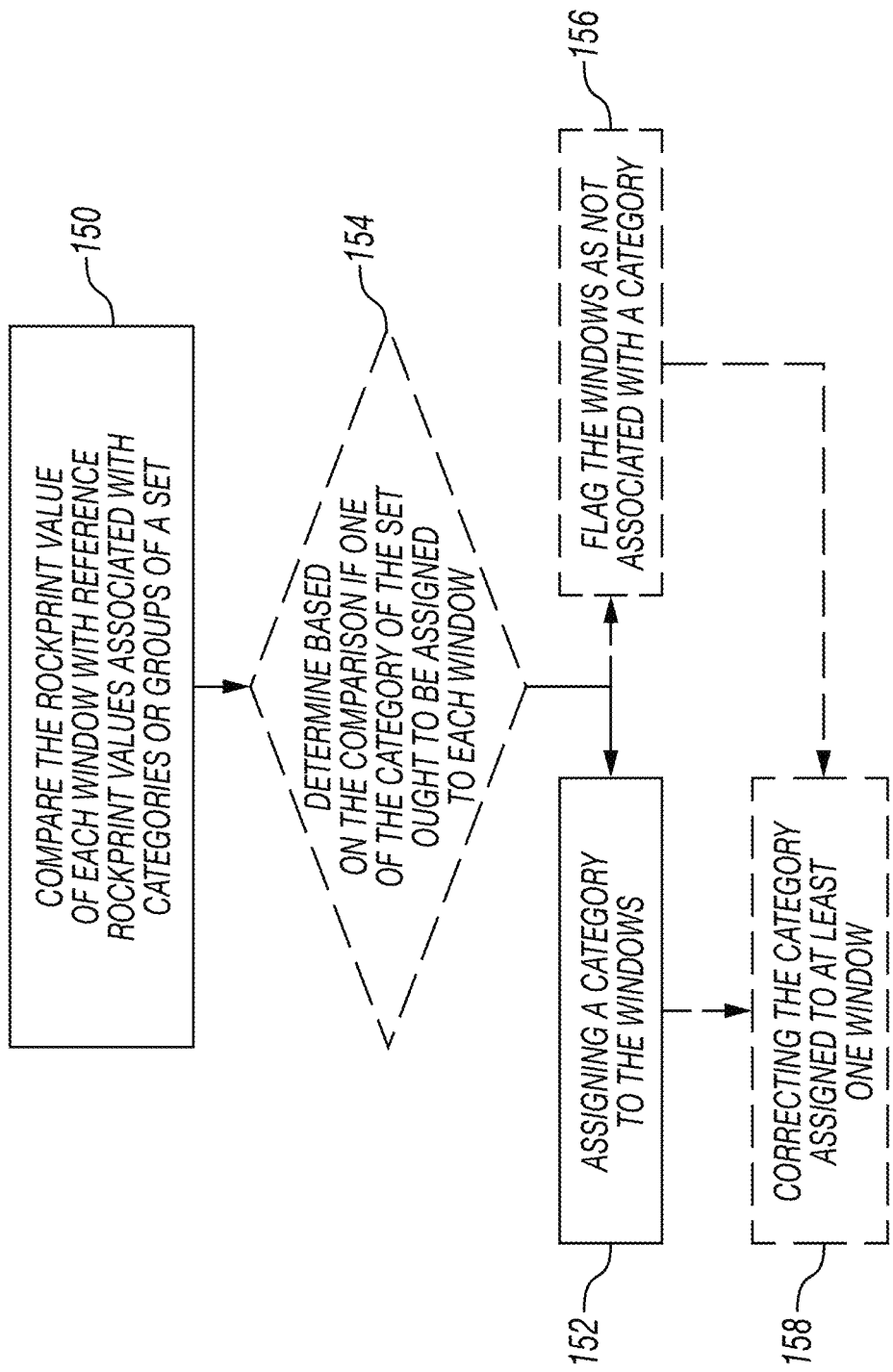
FIG. 2B is a flow diagram of an embodiment of the classification as per the method of FIG. 2A.
Figure 2C:
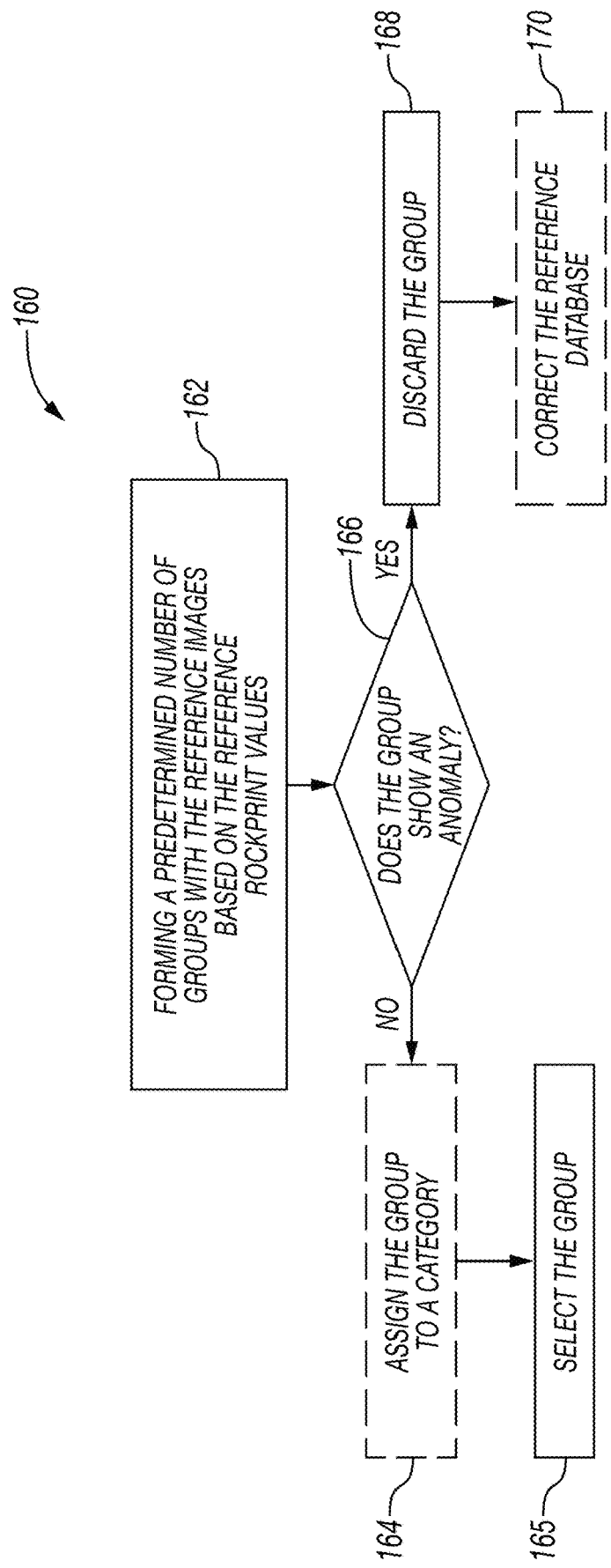
FIG. 2C is a flow diagram of a pre-processing the classification as per an embodiment of the method of FIG. 2A.

The classification may be supervised classification based on a comparison of the rockprint value of each window with rockprint values of images of reference rock samples for each category (block 150 on FIG. 2B). The image of reference rock samples (or reference images in the following) are stored in a database in a memory of at least one module of the calculator 56 in association with the category they are assigned to. The categories are the rock types of the rocks identified in each of the reference images. Examples of categories may be siltstones, sandstones, shales, etc. The reference images are preferably chosen so that there is one type of rock per image only. One category may also represent the background of the image in the case the totality of the image does not contain cuttings. In FIG. 4, for reasons of simplifying the schematics, the set of categories includes A, B and C, and one category is assigned to each window. For instance, in FIG. 4, category A has been assigned to windows 202 and 204 while category B has been assigned to window 206.

The reference rockprint values for each reference image may be obtained by defining windows in the reference images that have the same number of pixels and same shape than the predetermined windows as defined above and by computing the rockprint value for each window of the reference image. The rockprint values may then optionally be statistically processed in order to reduce the number of rockprint values representative of each category and reduce the computation time.

The comparison may include, for each window, calculating a likelihood for the window to be associated to each category. The likelihood may be based on a distance such as a Euclidian distance (or any other type of distance) from the rockprint value to the set of reference rockprint values representative of the category in the coordinate space of the rockprint. It may be noted that the likelihood of the window to be assigned to one category may be calculated also depending from the other categories of the set, the likelihood being representative of the chances of the window belonging to said category versus belonging to other categories of the set (that the sums of the likelihoods being equal to 100%). The likelihood for one category may also be calculated independently from the other categories, the likelihood then being representative of the chances of the window belonging to said category versus not belonging to said category. Any other known and appropriate classifier may be used for performing the comparison and the classification.

The classification may also include assigning to each window a category based on the comparison (block 152). For the example above, the assigned category may be the one for which the maximum likelihood has been obtained.

Alternatively, the classification may be a non-supervised classification. In this case, the method comprises beforehand a pre-processing 160 represented on FIG. 2C. The pre-processing may be performed at any time before classification of the image. It can be performed after each update of the set of reference images, before the image is even taken, or alternatively for each image that is analyzed.

The pre-processing 160 includes forming a predetermined number of groups (block 162), each group containing reference images of the database, wherein the predetermined number of groups can be set by the user. In this case, instead of having one group per category (hence having a broad distribution), there may be several groups (each having a narrow distribution) per category. It will enable to identify more precisely each type of rock within one category. For instance, one group may be a siltstone that contain a lot of quartz while another one group will identify siltstones comprising micas in majority, the cuttings on the image not having the same color and/or texture property whereas they belong to the same category. The groups are not predetermined or labelled by the operator, they are formed only taking into account the features of each of the windows in the database. In an embodiment, the groups are formed for each category, with the images associated to the category only. In another embodiment, the groups are formed taking into account all of the reference images and the categories may be assigned to each group depending on the images contained in the group. In the latest case, once the groups have been determined, they are associated to the category to which the reference images included in the group belong (block 164).

Such non-supervised classification enables an accurate classification as well as a quality check regarding the database. For instance, the method 160 may include testing if one group contains an anomaly (block 166), such as images belonging to several categories (when the groups are formed with the whole reference image set) or only one image. If the group is not an anomaly, it is selected (block 165) and taken into account for the following operations of the method. However, if the group is considered as an anomaly, the group may be discarded from consideration (block 168). Additionally, reference images belonging to the group may be investigated and the database may be corrected if needed (block 170). For instance, the images may be deleted from the database or the category assigned to one image may be corrected.

If the non-supervised classification is applied, the comparison at block 150 may include, for each window, calculating a likelihood for the window to be associated to each group and determining the category at block 152 may include assigning to each window the category associated with the group corresponding to the maximum likelihood. Alternatively, the likelihood for the image belonging to each category is assessed, by summing the likelihood of belonging to each group associated with said category, and the window is assigned the category for which the likelihood is maximum.

The classification may also include an optional operation of determining for each window that the window should not be associated to any category of the set (block 154). This may be determined by comparing the maximum likelihood to a first predetermined threshold. For instance, the first threshold value may be 50% when the likelihood is independent from the other categories. If the maximum likelihood is inferior to this threshold, it means that none of the category corresponds to the texture represented in this window. In this case, the window may be flagged as such (block 156). For instance, window 208 of the FIG. 4 in which a question mark is shown instead of a letter representative of a category is flagged as not assigned to any category. This operation may be useful in particular when one feature that is not rock (such as background surface) is represented on the image. It may also enable to identify a new type of rock sample that does not yet appear in the database.

The classification may also include correcting the category assigned to at least one window based on the categories assigned to the neighboring windows (block 158). This is as well an optional operation but that enables to optimize the classification. The neighboring windows may for instance be windows that are contacting the window and/or windows being at a distance inferior to a predetermined distance for the window. This operation may include comparing the likelihood of the association of the window to said category (ie the maximum likelihood) to a threshold and, if the likelihood is below the threshold (for instance 60%), verifying if the category is assigned to at least a predetermined portion of neighboring windows. For instance, if the neighboring windows selected for the operation are the 8 windows in direct contact with the window, the operation may verify that at least 4 of the 8 windows have the same category assigned to them.

If this is not the case, the correction may include modifying the category assigned to the window based on the likelihoods calculated for the window for each category and the categories assigned to each of the neighboring windows. On FIG. 4, for instance, a correction is applied to windows 210, 212 and 214. The category assigned to them has changed in view of the categories assigned to the surrounding windows.

The correction may also be applied to the windows that have been flagged as matching no category. For instance, as seen in FIG. 4, this correction is applied successfully to window 208 while it has not given any satisfactory output when applied to window 209.

Of course, the example criteria for launching the correction and performing the correction has been given as an example but any appropriate criteria might be chosen. A sum of the likelihoods of the window and the neighboring windows for the category might for instance be compared to the likelihood for the window of the currently assigned category.

The method may also include determining at least a property of the geological formation (block 120) based on the classification. The property includes the quantification of each type of rock in the sample, and therefore the lithology of the formation at a predetermined depth corresponding to the depth at which the sample has been cut from the formation. The property is derived directly from the classification. It may alternatively include a simple computation, ie calculating percentages of windows classified in each category among the windows classified in categories representative of rock types.

The method may also include assigning to the image an indicator representative of a confidence level of the classification, based on the likelihoods of the windows of the image and their associated category (block 122). The confidence level indicator may be based on the likelihoods for each of the windows and may for instance be an average of the likelihoods for each of the windows. In this case, the confidence level indicator for each window may also be plotted so that the windows for which the classification is the less confident can be identified. An example of confidence level indicator CL is the following: if a window is identified as a type A, a distance $d_{cluster\ A}$ (for example a normalized euclidean distance) from the rockprint vector of this window with the cluster of rockprint vectors for the corresponding A rock type in the database is computed. The likelihood $p_A$ given by the classifiers for the rock type A and obtained as mentioned above is multiplied by an attenuation function depending on the distance $d_{cluster\ A}$ (for example $e^{-x}$). The confidence level indicator may be mathematically expressed as follows: $CL = p_A * e^{-d_{cluster\ A}}$ This operation is an optional operation but enables to identify the portions of the images that may have not been well classified more easily. It is also to be noted that windows of the image that are identified as assigned to a category with a very high confidence level may be directly added to the database as reference images. On the contrary windows of the image that are not classified with a good confidence level may be re-examined by a geologist and included in the database as reference image in order to populate more accurately the reference database and therefore significantly improve the classification. The method may also comprise adding a window associated with a category as a reference image in the database (block 124). Adding windows in the database may be done automatically as a function of the confidence level. For instance, if the confidence level is greater than a predetermined threshold, the window may be automatically added as a reference image for the associated category in the reference database. On the contrary, if the window has a confidence level below a certain threshold, it may be displayed on the screen and input from the user may be requested. Then, the window may be included it in the reference database associated to the category validated by the user. In another embodiment, the user may directly select an area of the image, copy it and associate it with a category via the user interface. The area will then be added to the reference database as a reference image associated with the category selected by the user. When reference images have been added to the reference database, the classification may immediately be performed once again with the same image to analyze and the updated reference database in order to compute updated results for said image, as shown by arrow 126.

Figure 5:
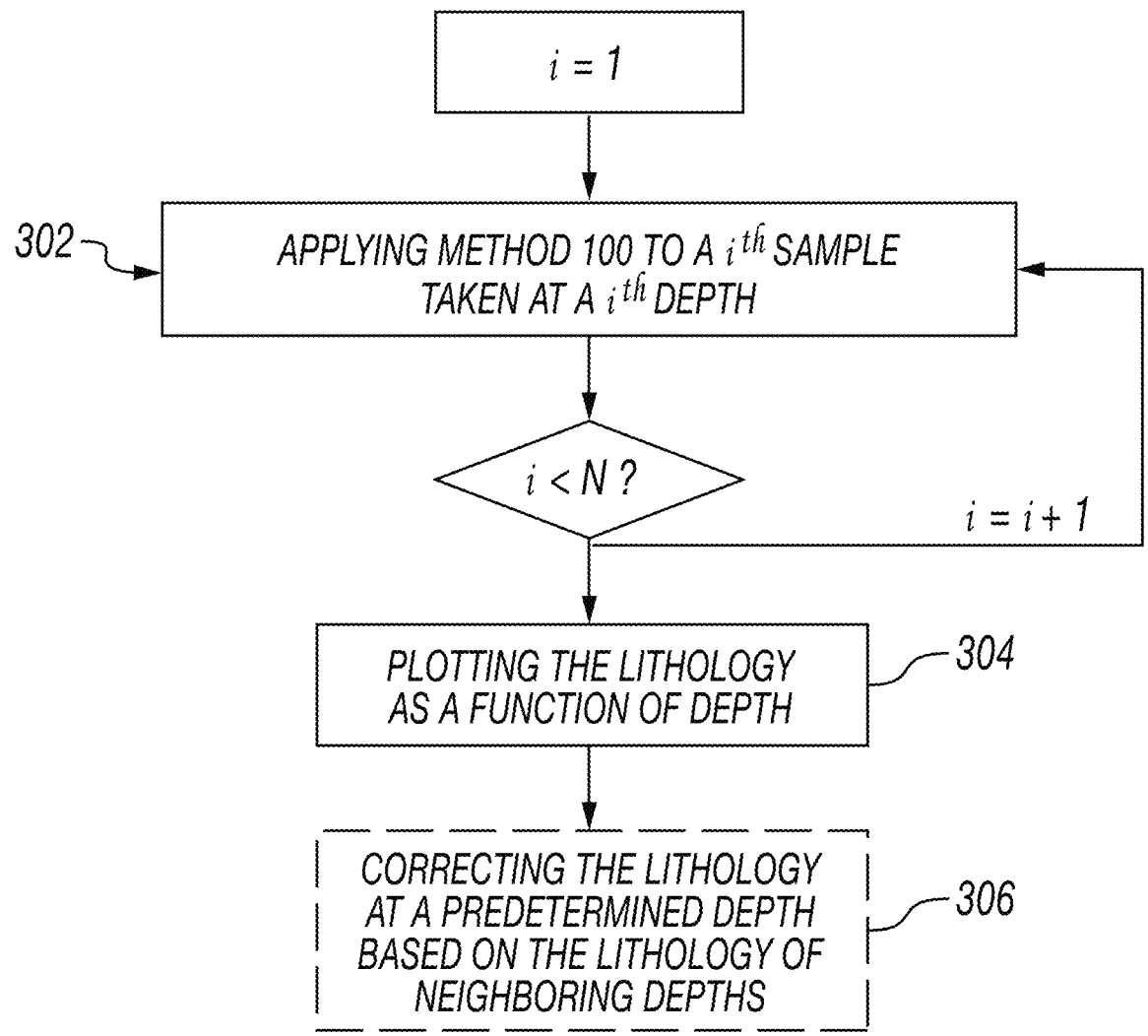
FIG. 5 is a flow diagram of a method according to another embodiment of the disclosure.

As shown in the flowchart of FIG. 5, the method according to an embodiment of the disclosure may be an iterative method 300 for obtaining lithology of a wellbore. This method is performed by one or more modules of the calculator. The method 300 comprises applying the method 100 of FIGS. 2A & 2B (and optionally 2C) to a set of N samples, taken at a plurality of depths, so that to cover the whole range of depths in a predetermined wellbore for example (block 302). When all of the sample have been collected, the method 300 may include plotting the derived lithology for each of the sample as a function of depth (block 304). In other words, the method may include collecting rock samples of the formation at different depths and plotting a profile of the lithology of the formation versus depth based on images of the different samples. Operation 304 may also include assigning to each image an indicator representative of a confidence level of the classification, based on the likelihoods of the windows of the image and their associated category, as indicated above, and plotting the confidence level indicator relative to depth.

Figure 6:
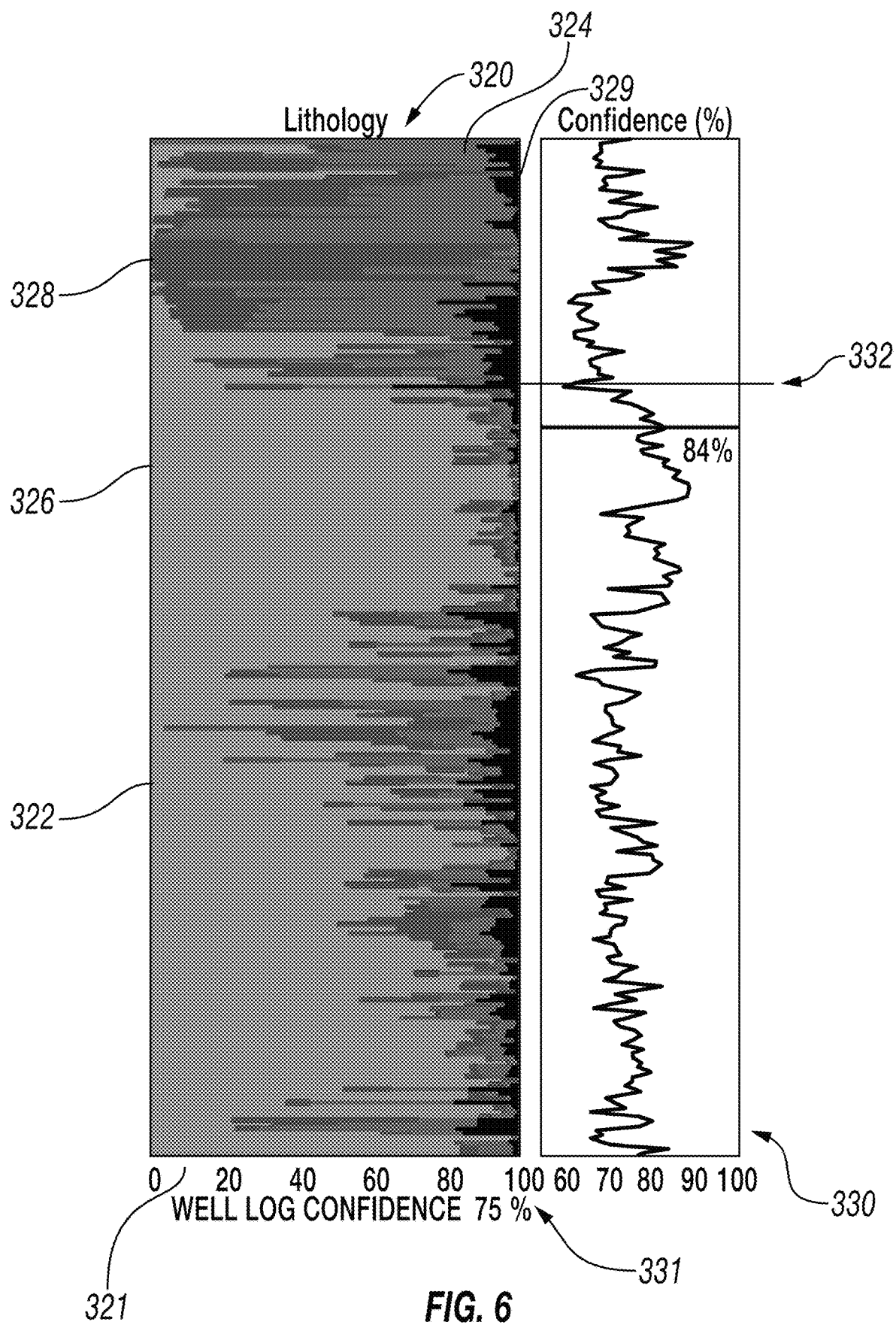
FIG. 6 is a plot showing an output of the method of FIG. 5.

FIG. 6 shows an output of the operation 304. Plot 320 represents the lithology as a function of depth, the percentage being shown in abscissa 321, while the depth is in ordinate 322. The colored zones of the plot each represent the types of rocks that have been detected on the images of the samples at the corresponding depth. Here, there are 4 categories, siltstone 324, sandstone 326 and shales 328. The "no match" category 329 is also shown on the plot. The output may also include the confidence level 330 corresponding to each of the sample as a function of depth. A well confidence level may also be computed as shown at 331. It is based on the average confidence level for the samples taken in the well.

The method 300 may also include correcting the lithology at each depth in function of the neighboring depths (block 306). Indeed, generally, lithology varies continuously in most of the wellbore. Therefore, based on the confidence level at each depth, depths having a lower confidence level may be compared to neighboring depths associated with a higher confidence level are corrected. For instance, at depth 332, it can be seen that result vary from the results at both depth above and depth below, that the confidence level is relatively low and that a high proportion of "no match" window has been detected. It is therefore possible to correct the results at this depth so that they match the neighboring results. The correction may for instance be applied to depths having a confidence level below a predetermined threshold and/or to the depths having a confidence level that is relatively low in view of the confidence level of the whole wells.

As explained above, the method is based on a rockprint describing the texture of each of the windows. The rockprint may be a predetermined rockprint or it may be a rockprint that has been selected among a plurality of potential rockprints, ie vectors comprising indicators representative of the windows' texture. A selected rockprint enables to adapt the classification to the database of reference images. Indeed, there might be dedicated databases for instance for several areas in the world or difference types of formation and all of the indicators do not capture with the same efficiency the features of the different types of rocks.

Therefore, the method may also comprise additional operation of selecting the rockprint. This additional operation is not performed at each image analysis, but generally when the database containing the reference images is built and then anytime it is modified. This operation may as well be performed by one or more modules of the calculator 56 based on instructions of a program stored in its memory and executed by a processor.

The selection of the rockprint is based on the values of each of the potential rockprints for a set of images of reference rock samples. It is performed by using known algorithm for feature selection, such as SFFS (Sequential Forward Floating Selection), SBFS (Sequential Backward Floating Selection) or GSBS (Generalized Sequential Backward Selection) algorithm or more generally any appropriate feature selection method. This enables to select the combination of indicators that will be the most efficient in differentiating the available categories of the set based on the references images of the current database. Each combination of indicator is a potential rockprint and the rockprint used in method 100 is the output of the feature selection algorithm.

Figure 7:
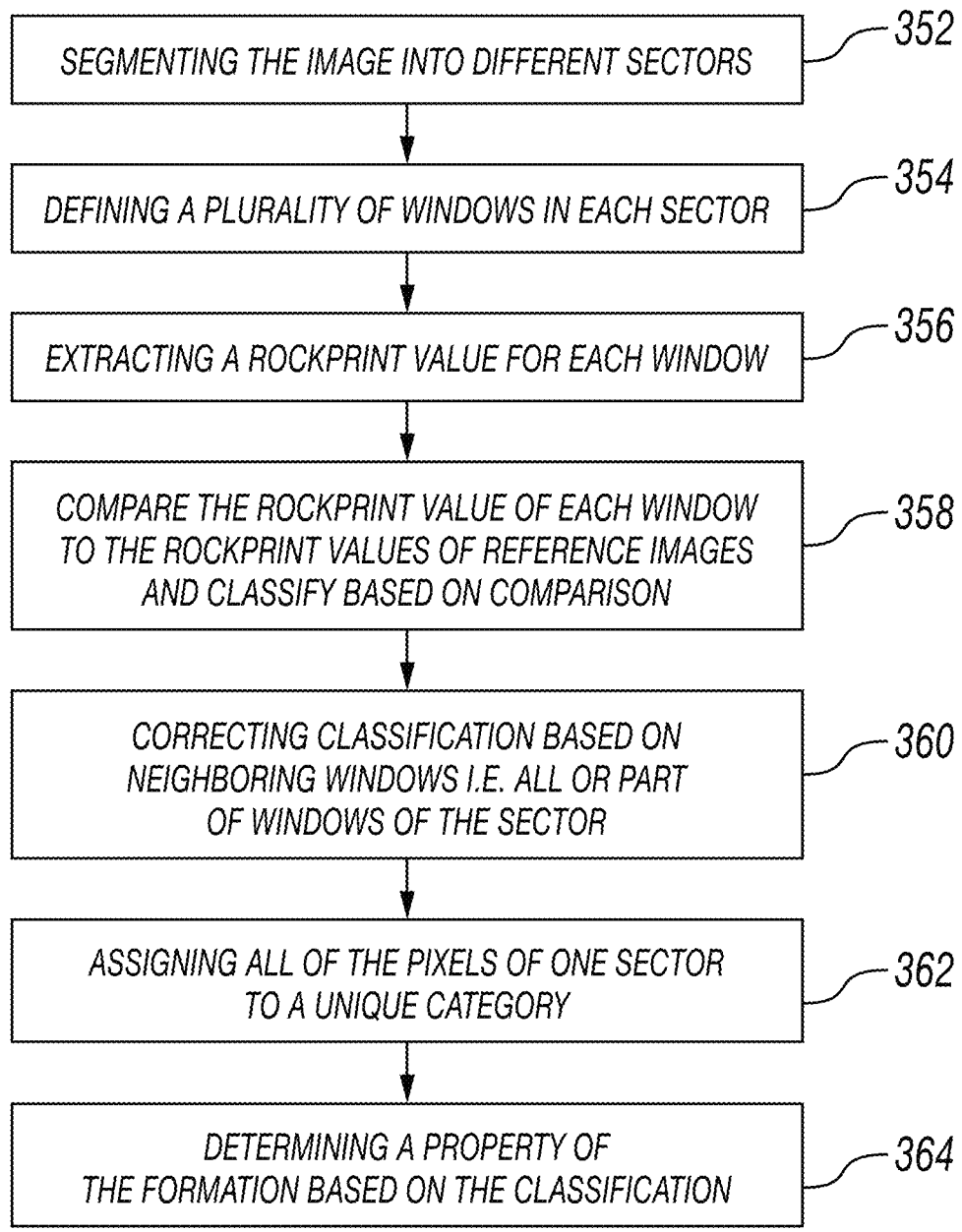
FIG. 7 is a flow diagram of a method according to another embodiment of the disclosure.

In another embodiment of the method, shown on FIG. 7, the image analysis 112 may comprise a first operation of segmenting the image according to one or several criteria, such as texture or color (block 352). The aim of the segmentation is to detect the boundaries of the different sectors of the image having different textures and/or colors. Methods for segmenting may be already known and any appropriate method for segmenting the image might be used such as Canny filters, Normalized Cuts method, etc. The output of the segmentation includes closed sectors with different boundaries, each sector having a unique texture and/or color type.

The segmentation may take place in one or several operations. For instance, the method may include a first segmentation operation using color and a second segmentation based on texture. The segmentation using color may be performed pixel per pixel using an algorithm such as a Watershed algorithm. This generally leads to a very sensitive segmentation so it can be considered gathering the adjacent sectors having similar average color. The second segmentation takes place in a sector whose boundaries are delimited by the first segmentation to make sure to discriminate two cuttings having similar color but different texture. The second segmentation may include extracting one or more rockprints (ie vectors comprising one or more indicators as explained above) for segmentation windows of the current sector and finding local maxima for the rock print gradient. The rockprint gradient is representative of the difference between the rockprint for one window and the rockprint of one or more adjacent windows. The segmentation windows may be chosen so that they match the windows as defined above for the classification in terms of shape and size in order to simplify the computation. However, they should be of different shape and size than the windows used for the classification. Depending on the local maxima value (if above a predetermined threshold) and/or location (if the local maxima extend continuously along a line), the sector may be divided in two or more sectors along the line defined corresponding to the local maxima. Of course, the above embodiment is only exemplary and any variant may be applied to the segmentation, for instance, using only one of the first and second segmentation or using alternative algorithms to the ones disclosed above to perform the segmentation.

Figure 8:
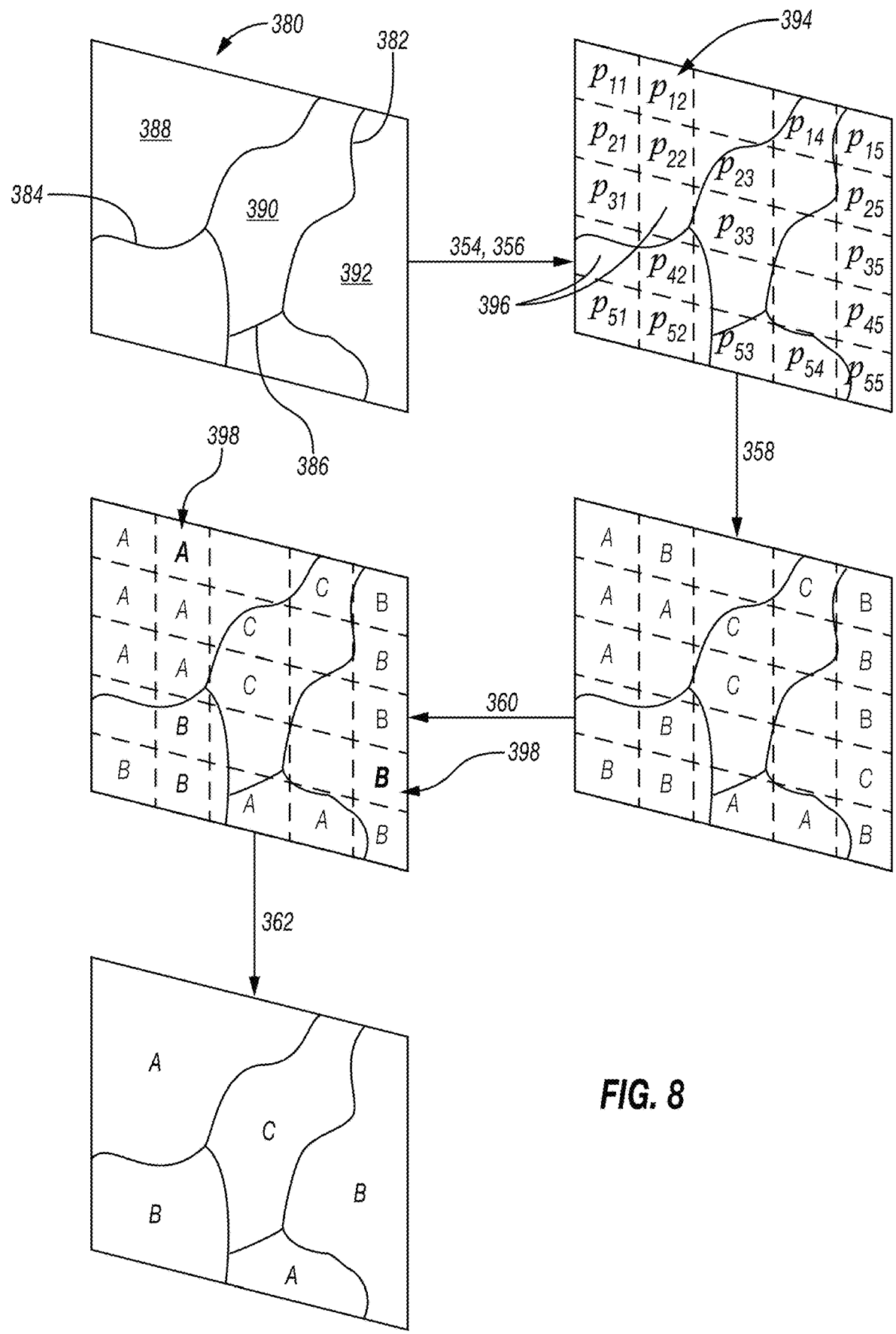
FIG. 8 is a schematic representation of several operations of the method, of FIG. 7

FIG. 8 shows an example of schematic representation of several operations of the method according to FIG. 7, including the segmentation and classification. The image 380 shows the segmented image. The segmentation delimits boundaries 382, 384, 386 for instance of different sectors such as 388, 390, 392 having texture and/or color features of one type therein.

Once the image has been segmented, the image analysis comprises defining a plurality of windows in the image as explained above in relationship with the embodiment of FIG. 2A (block 354). When the image has been segmented beforehand, the number of pixels in each window may be greater than when the image has not been segmented. Furthermore, the windows may be defined so that each window is contained entirely or almost entirely in one sector. In other words, the definition of the plurality of windows is performed so that each window is positioned in one sector only. Exemplary windows 394 are shown on FIG. 8. These windows are situated in one sector only so that the classification is more accurate. All of the pixels of the image might not be contained in one of the examined window, especially pixels situated at the edges of the sector may be discarded. In other words, the windows are selected so that they contain pixels situated only in one sector and so that each of the pixel of the window are at least at a predetermined distance from the boundaries of the sector. In the embodiment of FIG. 8, the windows have been pre-determined before sectors definition and window definition is a window selection: some windows 396 are not taken into account as substantial parts of it are in different sectors. On the contrary, the location of the windows may be selected as a function of the sector's boundaries once the boundaries are known.

The method then comprises extracting a rockprint value for each window (block 356) and compare its rockprint value with rockprint values of reference images (block 358) as also explained in relationship with FIG. 2A in order to classify each of the window. A category is therefore assigned to each window.

In this embodiment, the classification may also include a correction of the classification of a window using neighboring windows (block 360). In this case, the neighboring windows are all or part of the windows of the sector taking into account all of the windows in the same sector. The correction may be performed so that all of the windows defined into a sector are assigned to the same category after the correction operation. This operation is optional. It is shown on FIG. 8 that windows 398 have been corrected as a function of the windows situated in the same sector.

The method may also include assigning to all of the pixels of the sector a unique category, this unique category being determined during the correction operation (block 362). Therefore, the pixels that do not belong to any window but belong to the sector are assigned to a category, for instance the category determined for all the windows of the sector at the correction operation. This operation may be performed via stretching, ie extending to all of the pixels of the sector the classification that has been obtained for the windows selected for such sector.

The method then includes determining a property of the formation based on the classification (block 364), ie the lithology at the depth at which the sample has been collected, as indicated in relationship with the first embodiment.

The method 100 or 300 may also include extracting from the reference database one or more reference images that are the images considered as the closest images from each window or for the windows of the image belonging to one group and/or one category. The closest reference image may be selected as the image for which the maximum likelihood is found with the currently analyzed window. This may be particularly beneficial when the non-supervised classification technique is used as the groups are small and these closest reference images may be extracted and displayed faster. This enables to the user to check the quality of the classification. This can be performed automatically or only at user's request for a window for which he wants to perform additional checks.

Further, the extracted reference images may be associated with meta-data, that can include location or depth at which such image was taken, additional measurements that were taken on the cuttings corresponding to the closest reference image, in order to give additional information regarding the selected window. Of course, the reference images may be pulled out of the database only if appropriate permission has been given. For instance, the reference image and associated meta-data might be displayed only if the meta-data indicate that the reference image has been taken for the same client that the one for which the current job is being performed.

When images taken at other wells have been registered and after lithology has been obtained, it is also possible to extract images with close lithology with associated meta-data from the well from which the image is coming, in order to facilitate and guide the user interpretation.

Several embodiments of the method have been described hereinabove but the embodiments do not limit the scope of the claims. For instance, the analysis of the image according to the embodiment of FIG. 7 may also comprise determining "No Match" windows, as disclosed in relationship with FIGS. 2A & 2B. The classification may also be supervised or non-supervised and/or comprise additional operations.

Figure 9:
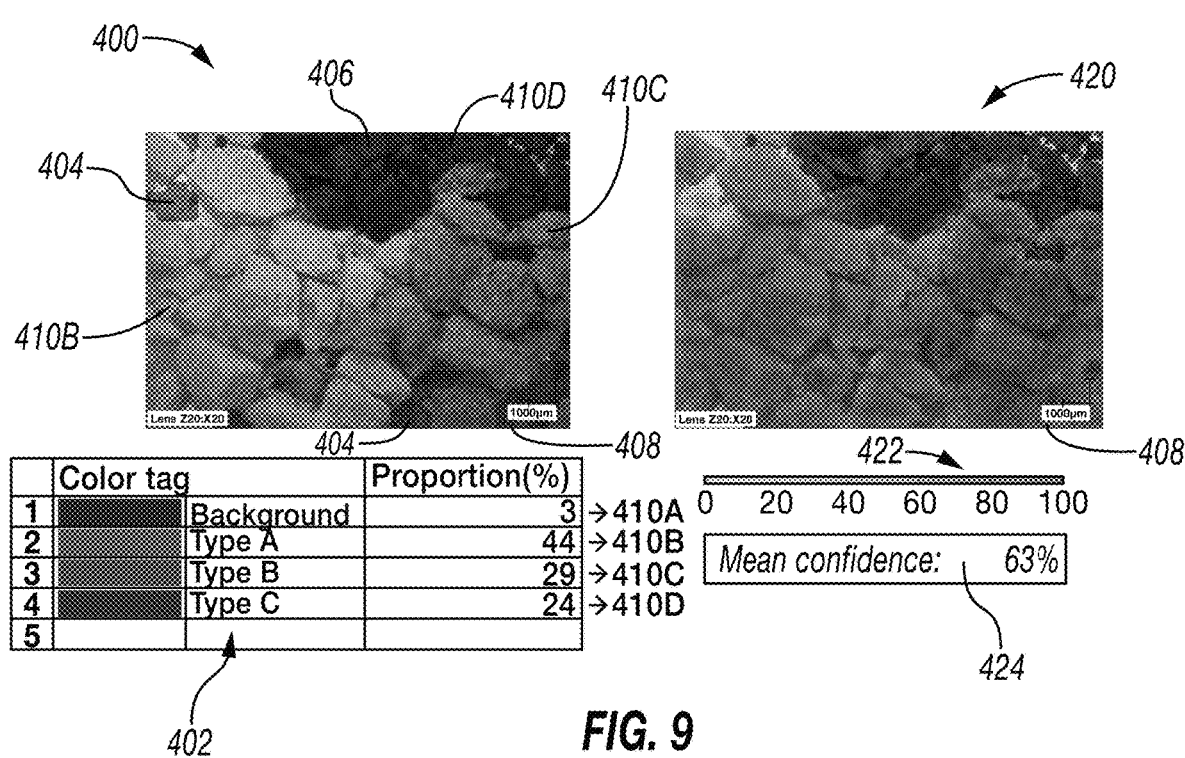
FIG. 9 shows outputs of a method according to an embodiment of the disclosure when the input to the method is FIG. 3

FIG. 9 shows the outputs according to an embodiment of the method including the operation 122. The input to the method is image 108 of FIG. 3. It can be seen that on FIG. 3 there are 3 types of cuttings that are gathered in different zones 111A, 111B, 111C of the image delineated by dotted lines. Background 109 is also visible.

FIG. 9 shows on the left-hand side image 400 the classification obtained by an embodiment of the method. Image 400 shows a superposition of the initial image with color for classifying each portion of the image according to the type of rock appearing on the image. The legend 402 indicates which color is associated with which category 410A, 410B, 410C, 410D. On this image, 3 rock categories are detected, as well as the background to identify the portions of the images that do not contain any cuttings. Image 400 gives a first good estimation of the rock types and lithology as it can be seen that cuttings of different types are classified in different categories and the classification enables a rather correct delimitation of the cuttings. For instance, delimitation of cuttings 404 or 406 is clearly shown. However, there are still a few portions of the image (see 408 for instance) in which the classification seems to not be performed correctly, probably because in this portion there are cuttings of small size on background. However, these portions are of relatively small size and the results of the classification are therefore satisfactory.

To be able to more clearly analyze the output of the classification, the output also includes an image 420 on the right-hand side of FIG. 4 showing a confidence level for all of the windows of the image to be compared with the legend 422. This confidence level is generally good but it can be seen that several windows have been determined with less confidence especially regarding the zone 408 and/or the cuttings edges and/or the markings added to the image. It enables to verify if there are portions of the image that should be double-checked and what are the types of cuttings that are not well-detected at the moment, to further populate the reference database. Furthermore, the output includes a confidence level 424 for the entire image (average of the confidence level for each of the windows). It can be seen that most of the image has been categorized with a confidence level that is relatively high.

The disclosure relates to a method for determining at least a property of a geological formation based on an optical image of at least a rock sample taken from the formation, wherein the image comprises a plurality of pixels. The method comprises defining a plurality of windows in the image, wherein each window comprises predetermined number of pixels and is of a predetermined shape, and, then, for each window, extracting a rockprint value representative of the window, wherein the rockprint comprises at least one indicator for characterizing a texture of the window. It also includes classifying the windows of the image into categories of a predetermined set of categories, wherein each category is representative of one type of rock, wherein the classification is based on a comparison of the rockprint value of each window with rockprint values of images of reference rock samples for each category, and, based on the classification, determining the at least one property of the geological formation, wherein the property includes the quantification of each type of rock in the sample.

The method may also comprise segmenting the image into several sectors, wherein each sector of the image is defined by a closed boundary. Segmenting the image may comprise performing a first segmentation based on color of the image and a second segmentation in each sector defined as an output of the first segmentation based on texture in the sector or any other appropriate segmentation or combination of segmentations. When the image is segmented, the definition of the plurality of windows may be performed so that each window is positioned in one sector only. In particular, the definition of the plurality of window is performed so that each window is at least at a predetermined distance from the boundaries of the sector. The segmentation may therefore be performed before the classification. When the image is segmented, the classification may also be configured to classify all the pixels of one sector in a unique category.

The method may also include defining the rockprint among a plurality of potential rockprints based on the values of each of the potential rockprints for a set of images of reference rock samples. The rockprint selection may be for instance performed when the set of images of references rock samples is modified.

In an embodiment, the rockprint values of images of the reference rock samples are obtained by defining windows in the reference images, wherein each window comprise the predetermined number of pixels and the predetermined shape.

In an embodiment, the classification includes, for a predetermined window, calculating based on the comparison a likelihood for the window to be associated to each category. In particular, the classification may include assigning to each window the category for which the maximum likelihood has been obtained.

In another embodiment, the method includes pre-processing the reference images in order to determine groups of the reference images, wherein each of the group is associated to a category. The groups may be formed within images belonging to a category or may be formed within all of the reference images. In the latest case, assigning a category to the group includes assigning the category of the images contained in the group. The classification may include, for a predetermined window, calculating based on the comparison a likelihood for the window to be associated to each group. The classification may in particular include assigning to each window the category assigned to the group for which the maximum likelihood has been obtained and/or the category for which the maximum likelihood has been obtained. The likelihood for each category may be computed from the sum of likelihood of the groups associated to the category.

In the preceding embodiment, the pre-processing may include verifying if each group shows an anomaly and discarding the group showing an anomaly so that it is not used for the classification. The anomaly may be for instance one of the following: the group contains images associated to several categories, or the group contains a number of images that is below a predetermined threshold.

In an embodiment, the classification includes determining that the window is not associated to any category of the set.

In an embodiment, the classification includes correcting the category assigned to at least one window based on the categories assigned to the neighboring windows. In this embodiment, when the method also comprises segmenting the image into several sectors, wherein each sector of the image is defined by a closed boundary, the neighboring windows may be all or part of the windows defined in the same sector as the at least one window.

In an embodiment, the method comprises assigning to the image an indicator representative of a confidence level of the classification, based on the likelihoods of the windows of the image and their associated category.

In an embodiment, the method includes using one or more windows as images of reference rock samples and performing a subsequent classification based on the updated set of images of reference rock sample.

The method may also comprise collecting rock samples of the formation at different depths and plotting a profile of the lithology of the formation versus depth based on images of the different samples. In this case, the method may include correcting the quantification associated to a depth as a function based on the neighboring depths. The correction may be performed by assigning to each image an indicator representative of a confidence level of the classification, based on the likelihoods of the windows of the image and their associated category, and plotting the confidence level indicator relative to depth wherein the correction is applied at a predetermined depth based on a confidence level at said depth.

The rock sample may be drill cuttings.

The disclosure also relates to a system for determining at least a property of a geological formation based on an optical image of at least a rock sample taken from the formation, wherein the image comprises a plurality of pixels. The system comprising a calculator comprising one or more modules having at least a processor, wherein the calculator is configured to define a plurality of windows in the image, wherein each window comprises predetermined number of pixels and is of a predetermined shape, for each window, extract a rockprint value representative of the window, wherein the rockprint comprises at least one indicator for characterizing a texture of the window, classify the windows of the image into categories of a predetermined set of categories, wherein each category is representative of one type of rock, wherein the classification is based on a comparison of the rockprint value of each window with rockprint values of images of reference rock samples for each category, and, based on the classification, determine the at least one property of the geological formation, wherein the property includes the quantification of each type of rock in the sample.

The system may also include an imaging device for taking an optical image of the rock sample.

The calculator may be configured to perform all or part of the embodiments of the method as disclosed herein above.

The disclosure also relates to a computer program for determining at least a property of a geological formation based on an optical image of at least a rock sample taken from the formation, wherein the image comprises a plurality of pixels, wherein the computer program comprises machine readable instructions to define a plurality of windows in the image, wherein each window comprises predetermined number of pixels and is of a predetermined shape; for each window, extract a rockprint value representative of the window, wherein the rockprint comprises at least one indicator for characterizing a texture of the window; classify the windows of the image into categories of a predetermined set of categories, wherein each category is representative of one type of rock, wherein the classification is based on a comparison of the rockprint value of each window with rockprint values of images of reference rock samples for each category, and, based on the classification, determine the at least one property of the geological formation, wherein the property includes the quantification of each type of rock in the sample. The computer program may comprise instructions to perform all or parts of the operations disclosed in relationship with the method disclosed hereinabove. The disclosure also relates to a computer readable medium storing the computer program as defined hereinabove.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the implementations introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to permit the reader to quickly ascertain the nature of the technical disclosure. It is submitted with the understanding that it will not be used to interpret or limit the scope or meaning of the claims.

The invention claimed is:

1. A method for determining at least a property of a geological formation based on an optical image of at least a rock sample taken from the formation, wherein the image comprises a plurality of pixels, the method comprising:
    defining a plurality of windows in the image, wherein each window comprises predetermined number of pixels and is of a predetermined shape,
    for each window, extracting a rockprint value representative of the window, wherein the rockprint comprises at least one indicator for characterizing a texture of the window,
    classifying the windows of the image into categories of a predetermined set of categories, wherein each category is representative of one type of rock, wherein the classification is based on a comparison of the rockprint value of each window with rockprint values of images of reference rock samples for each category,
    based on the classification, determining the at least one property of the geological formation, wherein the property includes the quantification of each type of rock in the sample.

2. The method according to claim 1, wherein it comprises segmenting the image into several sectors, wherein each sector of the image is defined by a closed boundary.

3. The method according to claim 2, wherein segmenting the image comprises performing a first segmentation based on color of the image and a second segmentation in each sector defined as an output of the first segmentation based on texture in the sector.

4. The method according to claim 2, wherein the definition of the plurality of windows is performed so that each window is positioned in one sector only.

5. The method according to claim 4, wherein the definition of the plurality of window is performed so that each window is at least at a predetermined distance from the boundaries of the sector.

6. The method according to claim 2, wherein the classification is configured to classify all the pixels of one sector in an unique category.

7. The method according to claim 1, wherein the rockprint values of images of the reference rock samples are obtained by defining windows in the reference images, wherein each window comprise the predetermined number of pixels and the predetermined shape.

8. The method according to claim 1, wherein the classification includes, for a predetermined window, calculating based on the comparison a likelihood for the window to be associated to each category.

9. The method of claim 8, wherein the classification includes assigning to each window the category for which the maximum likelihood has been obtained.

10. The method according to claim 1, including pre-processing the reference images in order to determine groups of the reference images, wherein each of the group is associated to a category, wherein the classification includes, for a predetermined window, calculating based on the comparison a likelihood for the window to be associated to each group.

11. The method of claim 10, wherein the pre-processing includes:
verifying if each group shows an anomaly, wherein the anomaly is one of the following:
The group contains images associated to several categories, or
The group contains a number of images that is below a predetermined threshold, and discarding the group showing an anomaly so that it is not used for the classification.

12. The method of claim 1, wherein the classification includes correcting the category assigned to at least one window based on the categories assigned to the neighboring windows.

13. The method of claim 12, wherein it comprises segmenting the image into several sectors, wherein each sector of the image is defined by a closed boundary wherein the neighboring windows are all or part of the windows defined in the same sector as the at least one window.

14. The method of claim 1, comprising assigning to the image an indicator representative of a confidence level of the classification, based on the likelihoods of the windows of the image and their associated category.

15. The method of claim 1, comprising using one or more windows as images of reference rock samples and performing a subsequent classification based on the updated set of images of reference rock samples.

16. The method of claim 1, comprising collecting rock samples of the formation at different depths and plotting a profile of the lithology of the formation versus depth based on images of the different samples.

17. The method of claim 1, where in the rock sample comprises drill cuttings.

18. A system for determining at least a property of a geological formation based on an optical image of at least a rock sample taken from the formation, wherein the image comprises a plurality of pixels, the system comprising a calculator comprising one or more modules having at least a processor, wherein the calculator is configured to:
define a plurality of windows in the image, wherein each window comprises predetermined number of pixels and is of a predetermined shape,
for each window, extract a rockprint value representative of the window, wherein the rockprint comprises at least one indicator for characterizing a texture of the window,
classify the windows of the image into categories of a predetermined set of categories, wherein each category is representative of one type of rock, wherein the classification is based on a comparison of the rockprint value of each window with rockprint values of images of reference rock samples for each category,
based on the classification, determine the at least one property of the geological formation, wherein the property includes the quantification of each type of rock in the sample.

19. The system of claim 18, including an imaging device for taking an optical image of the rock sample.

20. A non-transitory computer-readable medium for determining at least a property of a geological formation based on an optical image of at least a rock sample taken from the formation, wherein the image comprises a plurality of pixels, wherein the non-transitory computer-readable medium stores machine readable instructions to:
define a plurality of windows in the image, wherein each window comprises predetermined number of pixels and is of a predetermined shape,
for each window, extract a rockprint value representative of the window, wherein the rockprint comprises at least one indicator for characterizing a texture of the window,
classify the windows of the image into categories of a predetermined set of categories, wherein each category is representative of one type of rock, wherein the classification is based on a comparison of the rockprint value of each window with rockprint values of images of reference rock samples for each category,
based on the classification, determine the at least one property of the geological formation, wherein the property includes the quantification of each type of rock in the sample.

* * * * *